United States Patent [19]

Hayashi et al.

[11] 4,368,286
[45] Jan. 11, 1983

[54] THERMOPLASTIC POLYESTER RESIN COMPOSITION WHICH IS QUICKLY CRYSTALLIZABLE

[75] Inventors: Masahiro Hayashi; Tamotsu Yoshimura, both of Machida; Seiichi Mukai; Masaharu Shikama, both of Kawasaki; Hideto Kusumoto, Machida; Hideki Yamanouchi, Tokyo, all of Japan

[73] Assignee: Mitsubishi Chemical Industries Ltd., Tokyo, Japan

[21] Appl. No.: 244,875

[22] Filed: Mar. 18, 1981

[30] Foreign Application Priority Data

Apr. 1, 1980 [JP] Japan .................. 55-42250

[51] Int. Cl.$^3$ .................. C08G 63/02; C08K 5/09
[52] U.S. Cl. .................. 524/394; 524/601; 524/605
[58] Field of Search .................. 525/4, 5; 260/22 R, 260/22 A; 524/394, 601, 605

[56] References Cited

U.S. PATENT DOCUMENTS

| 3,207,739 | 9/1965 | Wales | 525/4 |
|---|---|---|---|
| 3,268,499 | 8/1966 | Wales | 525/4 |
| 3,327,020 | 6/1967 | Binsbergen | 525/4 |
| 3,367,926 | 2/1968 | Voeks | 525/4 |
| 3,575,931 | 4/1971 | Sherman | 525/5 |
| 3,575,931 | 4/1971 | Sherman | 260/28 |
| 3,960,807 | 6/1976 | McTaggart | 525/4 |
| 4,029,682 | 6/1977 | Foulks | 524/394 |
| 4,284,540 | 8/1981 | Iida et al. | 260/22 R |
| 4,327,007 | 4/1982 | Vanderkool et al. | 524/394 |

FOREIGN PATENT DOCUMENTS

| 2129162 | 10/1972 | France . | |
| 48-14425 | 5/1973 | Japan | 525/5 |
| 54-32561 | 3/1979 | Japan . | |

OTHER PUBLICATIONS

Chemical Abstracts, vol. 91, No. 12, Sep. 17, 1979, p. 37, Abstract 92482p; Columbus, Ohio, U.S.

*Primary Examiner*—Ronald W. Griffin
*Attorney, Agent, or Firm*—Oblon, Fisher, Spivak, McClelland & Maier

[57] ABSTRACT

A thermoplastic resin composition is quickly crystallizable and comprises 0.1 to 10 wt. parts of an alkali metal salt of higher fatty acid having carbon atoms of at least 26 obtained by an addition of a fatty acid to α-olefin having carbon atoms of at least 23 per 100 wt. parts of a thermoplastic polyester.

9 Claims, No Drawings

THERMOPLASTIC POLYESTER RESIN COMPOSITION WHICH IS QUICKLY CRYSTALLIZABLE

BACKGROUND OF THE INVENTION

1. Field of the Invention

The present invention relates to a thermoplastic polyester resin composition. More particularly, it relates to a thermoplastic polyester resin composition which is quickly crystallizable and comprises a specific crystallization accelerator in a thermoplastic polyester.

2. Description of the Prior Arts

Thermoplastic polyesters especially polyethyleneterephthalate are important as raw materials for preparing fibers, films and molded products. The thermoplastic polyesters have excellent characteristics such as high wearing resistance, excellent creep property and high dimensional accuracy because of partial crystalline structure. Therefore, thermoplastic polyesters are especially suitable for molded products to which severe mechanical stress is applied or which is heated at severe condition. Polyethyleneterephthalate, however has slow crystallization velocity requires relatively high temperature of a mold (about 140° C.) and relatively long time for pressing in preparation of a molded product. This is disadvantageous when preparing a molded product by an injection molding process.

Polybutyleneterephthalates have been commonly used as polyester resins for molding because of high crystallization velocity thereof. If the crystallization velocity is further increased, the molding cycle can be shortened to reduce production cost. This is remarkable advantage.

SUMMARY OF THE INVENTION

It is an object of the present invention to provide a thermoplastic polyester resin composition which has high crystallization velocity.

The foregoing and other objects of the present invention have been attained by providing a thermoplastic resin composition which is quickly crystallizable and comprises 0.1 to 10 wt. parts of an alkali metal salt of higher fatty acid having carbon atoms of at least 26 obtained by an addition of a fatty acid to $\alpha$-olefin having carbon atoms of at least 23 per 100 wt. parts of a thermoplastic polyester.

DETAILED DESCRIPTION OF THE PREFERRED EMBODIMENTS

Various crystallization accelerators for quickly crystallizing a thermoplastic polyester at high crystallization velocity have been studied to find the fact that certain alkali metal salts of higher fatty acid are remarkably effective as crystallization accelerators.

The thermoplastic polyesters used as one kind of the raw materials in the present invention can be polyethyleneterephthalates, polytrimethyleneterephthalates and polybutyleneterephthalate, or polyester derivatives thereof wherein terephthalic acid component or glycol component is partially, substituted by certain other comonomer component. Suitable comonomer components include at least one of bifunctional carboxylic acids such as isophthalic acid, naphthalenedicarboxylic acid, 4,4'-diphenoxyethanedicarboxylic acid, adipic acid and sebacic acid; and at least one of glycols such as ethyleneglycol, trimethyleneglycol, tetramethyleneglycol, hexamethyleneglycol, and decamethyleneglycol.

The thermoplastic polyester can be a mixture of two or more kinds of thermoplastic polyesters. Suitable thermoplastic polyesters include polyethyleneterephthalates, polyesters having at least 80 mol % of ethyleneterephthalate repeat units, polybutyleneterephthalates and polyesters having at least 80 mol % of butyleneterephthalate repeat units.

The thermoplastic polyesters usually have an intrinsic viscosity of 0.5 to 2.0 (in a mixed solvent of phenol and tetrachloroethane at 1:1 by weight; at 30° C.).

The alkali metal salts of higher fatty acid having carbon atoms of at least 26 preferably 30-400 which are used as the crystallization accelerator for thermoplastic polyesters in the present invention (hereinafter referring to as higher fatty acid salt) are produced by bonding an olefin having one double bond at a terminal (hereinafter referring to as $\alpha$-olefin) to a fatty acid by the conventional process (disclosed in Yukagaku Vol. 19, page 121, 1970) and heating the product in an aqueous solution of an alkali metal hydroxide to form alkali metal salts such as sodium, potassium and lithium salts.

The $\alpha$-olefin must have carbon atoms of at least 23. When a mixture of $\alpha$-olefins having different carbon atoms, the average carbon atoms must be at least 23. It is preferable to use a mixture of $\alpha$-olefins having average carbon atoms of at least 30 such as Dialene 30 TM commercially available by Mitsubishi Chemical Ind. (average carbon atoms of 43 measured by iodine value) and Dialene 208 TM commercially available by Mitsubishi Chemical Ind. (average carbon atoms of 23). The fatty acid is preferably propionic acid. The higher fatty acids obtained by bonding both components can be a mixture of $\alpha$-methyl fatty acids having carbon atoms of at least 33 (such as average carbon atoms of 46 measured by iodine value; referring to as $\alpha$-Fatty acid 30) and a mixture of $\alpha$-methyl fatty acids having carbon atoms of 23-31 (such as average carbon atoms of 26 measured by iodine value; referring to as $\alpha$-Fatty acid 208). The fatty acid is not limited to propionic acid and can be another fatty acid such as butyric acid, valeric acid.

In accordance with the present invention, 0.1 to 10 wt. parts of the higher fatty acid is incorporated to 100 wt. parts of the thermoplastic polyester. When the content of the higher fatty acid is less than 0.1 wt. part, the effect of the invention is not satisfactory attained whereas when it is more than 10 wt. parts, the mechanical property of the thermoplastic polyester as the matrix is inferior. These are disadvantageous. When a higher fatty acid salt having carbon atoms of less than 26 is incorporated, the side effect for thermal degradation of the thermoplastic polyester is disadvantageously found even though the same content as Na content of the higher fatty acid salt is incorporated in the thermoplastic polyester as shown in Reference.

In the preparation of the polyester resin composition, the crystallization accelerator is blended with the thermoplastic polyester and they are melted and mixed. The melt-mixing can be the conventional process using an extruder or the other desired machine.

In the composition of the present invention, it is possible to add a desired additive which is usually added, such as inorganic fillers, glass fibers and plasticizers. The additive can be added at any desired stage by a conventional manner.

The present invention will be further illustrated by certain examples and references which are provided for purposes of illustration only and are not intended to limit the present invention.

In the examples and references, an acid value was measured by Standard Oil and Fat Analysis Test method published by Nippon Yukagaku Kyokai (1978).

Preparation 1

Preparation of α-Fatty acid 30

Into a reactor, 167.5 g. of Dialene 30 (α-olefin having average carbon atoms of 43 manufactured and sold by Mitsubishi Chemical Ind.) and 185 g. of propionic acid were charged and the mixture was heated at 135° to 140° C. in nitrogen atmosphere and then, 9.2 g. of di-t-butyl peroxide was added dropwise during 4 hours and then, the mixture was stirred at the same temperature for 10 hours. The unreacted propionic acid was distilled off under a reduced pressure to obtain 178.6 g. of a mixture of higher fatty acids (average carbon atoms of 46) comprising α-methylmonocarboxylic acids having carbon atoms of at least 33 as main components. The product is referred to as α-Fatty acid 30. The α-Fatty acid 30 had an acid value of 38.7 KOH mg./g. and a melting point of 70° to 72° C.

Preparation 2

Preparation of α-Fatty acid 208

In accordance with the process of Preparation 1, except using Dialene 208 (α-olefin having average carbon atoms of 23 manufactured and sold by Mitsubishi Chemical Ind.) instead of Dialene 30, a higher fatty acid having average carbon atoms of 26, an acid value of 102.4 KOH mg./g. and a melting point of 52°–54° C. was produced. The product is referred to as α-Fatty acid 208.

Preparation 3

Preparation of α-Fatty acid 168

In accordance with the process of Preparation 1 except using Dialene 168 (α-olefin having average carbon atoms of 17 (16–18 carbon atoms manufactured and sold by Mitsubishi Chemical Ind.) instead of Dialene 30, a higher fatty acid having average carbon atoms of 20, an acid value of 179 KOH mg./g. and a melting point of 48°–50° C. was produced. The product is referred to as α-Fatty acid 168.

Preparation 4

Preparation of higher fatty acid salts

A mixture of 100 g. of α-Fatty acid 30 obtained in Preparation 1 and 10 ml. of xylene was heated to 140° C. and then, 9 g. of 30% aqueous solution of sodium hydroxide was added dropwise during about 1 hour under removing water out of the system by heating with stirring. After removing about 7.5 ml. of water, xylene was distilled off under a reduced pressure to obtain 115 g. of sodium salt of α-Fatty acid 30 (hereinafter referring to as α-Fatty acid salt 30).

In accordance with the above-mentioned process except using α-Fatty acid 208 or α-Fatty acid 168 instead of α-Fatty acid 30, the process was carried out to obtain sodium salt of α-Fatty acid 208 or sodium salt of α-Fatty acid 168 (hereinafter referring to as α-Fatty acid salt 208 and α-Fatty acid salt 168).

EXAMPLES 1 TO 6 AND REFERENCES 1 TO 7

Polyethyleneterephthalate ($[\eta]=0.66$) (NOVAPET manufactured and sold by Mitsubishi Chemical Ind.; hereinafter referring to as PET) and the higher fatty acid salts obtained in Preparation 4 and sodium stearate or sodium montanate were mechanically blended at ratios shown in Table 1 and each mixture was melted and mixed by a uniaxial extruder equipped with a Dulmage screw having a diameter of 20 mm (L/D=28) and the resulting strand was cooled in water and cut to form pellets. The pellet was tested by using a differential calorimeter (referring to as DSC; Perkin-Elmer IB type) by heating and cooling it to measure a crystallization temperature (Tcc) at heating and a melting temperature (Tm) and a crystallization temperature ($Tc^{300}$) at cooling after melting at 300° C. for 5 minutes.

When the crystallization velocity is higher, $Tc^{300}$ is higher and heat absorption peak on a DSC test paper for $Tc^{300}$ is sharp. In order to show the sharpness, a triangle along the heat absorption peak is drawn and an index of height/base of the triangle (the base of the triangle is the base line of the peak) is given.

When Tcc is higher, a melt fluidity of a polymer at a low temperature is higher and a molded product obtained by molding it in a low temperature mold has higher crystallinity.

When a sodium salt of relatively lower fatty acid is used, a thermal degradation of PET in a matrix is highly accelerated. The fact is studied in view of a stability of a resulting strand (stable melt spinning) and an intrinsic viscosity [η] which is measured in a mixed solvent of phenol/tetrachloroethane (1:1 by weight) at 30° C. The results of the examples and references are shown in Table 1.

Sodium montanate as one of higher fatty acid imparts excellent crystallization acceleration effect but it causes remarkable deterioration of thermal stability of PET as the matrix.

TABLE 1

| Example or Reference | Ref. 1 | Ref. 2 | Ref. 3 | Ref. 4 | Ref. 5 | Ref. 6 | Ref. 7 | Exp. 1 | Exp. 2 | Exp. 3 |
|---|---|---|---|---|---|---|---|---|---|---|
| Kind of crystallization accelerator | none | Na-stearate | Na-stearate | α-Fatty acid salt 168 | Na-montanate | Na-montanate | Na-montanate | α-Fatty acid salt 208 | α-Fatty acid salt 208 | α-Fatty acid salt 208 |
| Amount of the accelerator (wt. %) | 0 | 1 | 3 | 3 | 4 | 3 | 1 | 1 | 3 | 5 |
| Stability of strand* | O | O | X | Δ | — | — | — | O | O | O |
| [η] of strand | 0.602 | 0.497 | ‖ | 0.378 | 0.48 | 0.49 | 0.53 | 0.559 | 0.569 | 0.542 |
| Result by DSC: | | | ‖ | | | | | | | |
| Tcc (°C.) | 142 | 117 | ‖ | | 114 | 116 | 117 | 120 | 119 | 118 |
| Tm (°C.) | 259 | 260 | ‖ | 258 | 255 | 258 | 258 | 257 | 260 | 260 |
| $Tc^{300}$ (°C.) | 187 | 217 | ‖ | 219 | 215 | 213 | 211 | 211 | 218 | 220 |
| Ratio of height/base of peak | 1.3 | 5.1 | ‖ | 3.1 | — | — | — | 4.5 | 6.3 | 7.8 |

| Example or Reference | Exp. 4 | Exp. 5 | Exp. 6 |
|---|---|---|---|
| Kind of crystallization | α-Fatty | α-Fatty | α-Fatty |

TABLE 1-continued

|  | accelerator | acid salt 30 | acid salt 30 | acid salt 30 |
|---|---|---|---|---|
|  | Amount of the accelerator (wt. %) | 1 | 3 | 5 |
|  | Stability of strand* | O | O | O |
|  | [η] of strand | 0.562 | 0.615 | 0.548 |
|  | Result by DSC: |  |  |  |
|  | Tcc (°C.) | 121 | 123 | 121 |
|  | Tm (°C.) | 257 | 257 | 260 |
|  | Tc$^{300}$ (°C.) | 213 | 213 | 213 |
|  | Ratio of height/base of peak | 7.4 | 5.3 | 7.4 |

Note:
*Stability of strand:
O: A strand can be extruded in stable condition.
Δ: A strand is extruded in pulsation.
X: A strand is intermittently extruded.

EXAMPLES 7 TO 11 AND REFERENCES 8 TO 14

Polybutyleneterephthalate ([η]=1.10) (NOVADUR manufactured and sold by Mitsubishi Chemical Ind.: hereinafter referring to as PBT) and the higher fatty acid salts obtained in Preparation 4 and sodium stearate were mechanically blended at ratios shown in Table 2 and each mixture was melted and mixed by a uniaxial extruder equipped with a Dulmage screw having a diameter of 20 mm (L/D=28) and the resulting strand was cooled in water and cut to form pellets. The pellet was tested by using a differential calorimeter used in Examples 1 to 6. In Table 2, Tc is a peak value of the crystallization temperature measured by cooling it at 16° C./min. after heating at 10° C. higher than a melting point for 5 minutes. The intrinsic viscosity [η] is measured by the method of Examples 1 to 6.

TABLE 2

| Reference and Example | Kind of crystallization accelerator | Amount of accelerator (wt. %) | [η] | Tc (°C.) |
|---|---|---|---|---|
| Ref. 8 | None | 0 | 1.20 | 187 |
| Ref. 9 | None | 0 | 1.10 | 190 |
| Ref. 10 | None | 0 | 0.85 | 188 |
| Ref. 11 | Na-stearate | 1 | 0.96 | 206 |
| Ref. 12 | Na-stearate | 3 | 0.70 | 208 |
| Ref. 13 | Ca-stearate | 1 | 1.02 | 188 |
| Ref. 14 | Ca-stearate | 3 | 1.03 | 188 |
| Exp. 7 | α-Fatty acid salt 30 | 1 | 1.06 | 190 |
| Exp. 8 | α-Fatty acid salt 30 | 3 | 1.04 | 195 |
| Exp. 9 | α-Fatty acid salt 30 | 5 | 1.10 | 205 |
| Exp. 10 | α-Fatty acid salt 208 | 1 | 1.06 | 191 |
| Exp. 11 | α-Fatty acid salt 208 | 3 | 0.95 | 207 |

We claim:
1. A thermoplastic resin composition which is quickly crystallizable and comprises 0.1 to 10 wt. parts of an alkali metal salt of higher fatty acid having carbon atoms of at least 26 obtained by an addition of a fatty acid to α-olefin having carbon atoms of at least 23 per 100 wt. parts of a thermoplastic polyester.
2. The thermoplastic resin composition according to claim 1 wherein said α-olefin has carbon atoms of at least 30.
3. The thermoplastic resin composition according to claim 1 wherein said fatty acid is propionic acid, butyric acid or valeric acid.
4. The resin composition of claim 3 wherein said fatty acid is propionic acid and said α-olefin contains 43 carbon atoms on the average.
5. The resin composition of claim 3 wherein said fatty acid is propionic acid and said α-olefin contains 26 carbon atoms on the average.
6. The thermoplastic polyester resin composition according to claim 1 wherein said alkali metal salt of higher fatty acid has carbon atoms of 30 to 400.
7. The thermoplastic polyester resin composition according to claim 1 wherein said thermoplastic polyester is polyethyleneterephthalate or a polyester having at least 80 mol % of ethyleneterephthalate repeat units.
8. The thermoplastic polyester resin composition according to claim 1 wherein said thermoplastic polyester is polybutyleneterephthalate or a polyester having at least 80 mol % of butyleneterephthalate repeat units.
9. The thermoplastic polyester resin composition according to claim 1 wherein said alkali metal salt of higher fatty acid is sodium, potassium or lithium salt.

* * * * *